United States Patent
Türeci et al.

(10) Patent No.: US 6,232,460 B1
(45) Date of Patent: May 15, 2001

(54) ISOLATED NUCLEIC ACID MOLECULE WHICH ENCODES AN SCP-1 MUTEIN

(75) Inventors: Özlem Türeci; Ugur Sahin; Michael Pfreundschuh, all of Homburg/Saar (DE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/104,324

(22) Filed: Jun. 25, 1998

Related U.S. Application Data

(63) Continuation-in-part of application No. 08/892,702, filed on Jul. 15, 1997, now Pat. No. 5,888,751.

(51) Int. Cl.[7] ............................. C07H 21/02; C07H 21/04
(52) U.S. Cl. ......................................... 536/23.5; 536/23.1
(58) Field of Search ............................................. 536/23.1

(56) References Cited
PUBLICATIONS

Meuwissen et al., "Human Synaptonemal Complex Protein 1 (SCP1) Isolation and Characterization of the cDNA and Chromosomal Localization of the Gene," Genomics, 39:377–384 (1997).

Heyting et al., "Synaptonemal Complex Proteins," Genome, 31:81–87 (1987).

Sage et al., "cDNA Sequence of the Murine Synaptonemal Complex Protein 1 (SCP1)" Biochimica Biophipica Acta, 1263:259–260 (1995).

Meuwissen et al., "A Coiled Coil Related Protein Specific for Synapsed Regions of Meiotic Prophase Chromosome," EMBO J, 11(13):5091–5100 (1992).

Tureci et al., "Identification of a Meiosis–Specific Protien as a Member of the Class of Cancer/Testis Antigens," Proc. Natl. Acad. Sci. USA, 95:5211–5216 (1998).

*Primary Examiner*—Anthony C. Caputa
*Assistant Examiner*—Jennifer Nichols
(74) *Attorney, Agent, or Firm*—Fulbright & Jaworski, LLP

(57) ABSTRACT

The invention involves the recognition of a previously identified protein, SCP-1, as a marker for cell transformation. Diagnostic and therapeutic uses of this protein and related molecules are taught. Also disclosed is a method for identifying substances which are immunoreactive and indicative of pathological conditions, using normal cells as source material.

1 Claim, No Drawings

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 3393 base pairs
      (B) TYPE:   nucleic acid
      (C) STRANDEDNESS: double
      (D) TOPOLOGY:  linear (xi) SEQUENCE DESCRIPTION: SEQ ID NO: 1:

```
gccctcatag accgtttgtt gtagttcgcg tgggaacagc aacccacggt ttcccgatag      60
ttcttcaaag atatttacaa ccgtaacaga gaaatggaa  aagcaaaagc cctttgcatt     120
gttcgtacca ccgagatcaa gcagcagtca ggtgtctgcg gtgaaacctc agaccctggg    180
aggcgattcc actttcttca agagtttcaa caaatgtact gaagatgatt tggagtttcc    240
atttgcaaag actaatctct ccaaaaatgg ggaaaacatt gattcagatc ctgctttaca    300
aaaagttaat ttcttgcccg tgcttgagca ggttggtaat tctgactgtc actatcagga    360
aggactaaaa gactctgatt tggagaattc agagggattg agcagagtgt tttcaaaact    420
gtataaggag gctgaaaaga taaaaaaatg gaaagtaagt acagaagctg aactgagaca    480
gaaagaaagt aagttgcaag aaaacagaaa gataattgaa gcacagcgaa aagccattca    540
ggaactgcaa tttggaaatg aaaaagtaag tttgaaatta gaagaaggaa tacaagaaaa    600
taaagattta ataaaagaga ataatgccac aaggcattta tgtaatctac tcaaagaaac    660
ctgtgctaga tctgcagaaa agacaaagaa atatgaatat gaacgggaag aaaccaggca    720
agtttatatg gatctaaata ataacattga gaaaatgata acagctcatg gggaacttcg    780
```

```
tgtgcaagct gagaattcca gactggaaat gcattttaag ttaaaggaag attatgaaaa    840
aatccaacac cttgaacaag aatacaagaa ggaaataaat gacaaggaaa agcaggtatc    900
actactattg atccaaatca ctgagaaaga aaataaaatg aaagatttaa catttctgct    960
agaggaatcc agagataaag ttaatcaatt agaggaaaag acaaaattac agagtgaaaa   1020
cttaaaacaa tcaattgaga aacagcatca tttgactaaa gaactagaag atattaaagt   1080
gtcattacaa agaagtgtga gtactcaaaa ggctttagag gaagatttac agatagcaac   1140
aaaaacaatt tgtcagctaa ctgaagaaaa agaaactcaa atggaagaat ctaataaagc   1200
tagagctgct cattcgtttg tggttactga atttgaaact actgtctgca gcttggaaga   1260
attattgaga acagaacagc aaagattgga aaaaaatgaa gatcaattga aaatacttac   1320
catggagctt caaagaaat caagtgagct ggaagagatg actaagctta caaataacaa   1380
agaagtagaa cttgaagaat tgaaaaagt cttgggagaa aggaaacac ttttatatga   1440
aaataaacaa tttgagaaga ttgctgaaga attaaaagga acagaacaag aactaattgg   1500
tcttctccaa gccagagaga agaagtaca tgatttggaa atacagttaa ctgccattac   1560
cacaagtgaa cagtattatt caaagaggt taagatcta aaaactgagc ttgaaaacga   1620
gaagcttaag aatactgaat taacttcaca ctgcaacaag cttcactag aaaacaaga   1680
gctcacacag gaaacaagtg atatgaccct agaactcaag aatcagcaag aagatattaa   1740
taataacaaa agcaagaag aaggatgtt gaaacaaata gaaatcttc aagaaacaga   1800
aacccaatta agaaatgaac tagaatatgt gagagaagag ctaaaacaga aaagagatga   1860
agttaaatgt aaattggaca agagtgaaga aaattgtaac aatttaagga acaagttga   1920
aaataaaaac aagtatattg aagaacttca gcaggagaat aaggccttga aaaaaaagg   1980
tacagcagaa agcaagcaac tgaatgttta tgagataaag gtcaataaat tagagttaga   2040
actagaaagt gccaaacaga aatttggaga aatcacagac acctatcaga agaaattga   2100
ggacaaaaag atatcagaag aaaatctttt ggaagaggtt gagaaagcaa agtaatagc   2160
tgatgaagca gtaaaattac agaaagaaat tgataagcga tgtcaacata aatagctga   2220
aatggtagca cttatggaaa acataagca ccaatatgat aagatcattg aagaaagaga   2280
ctcagaatta ggactttata agagcaaaga acaagaacag tcatcactga gagcatcttt   2340
ggagattgaa ctatccaatc tcaaagctga acttttgtct gttaagaagc aacttgaaat   2400
agaaagagaa gagaaggaaa aactcaaaag agaggcaaaa gaaaacacag ctactcttaa   2460
agaaaaaaaa gacaagaaaa cacaaacatt tttattggaa acacctgaaa tttattggaa   2520
attggattct aaagcagttc cttcacaaac tgtatctcga aatttcacat cagttgatca   2580
tggcatatcc aaagataaaa gagactatct gtggacatct gccaaaaata ctttatctac   2640
accattgcca aaggcatata cagtgaagac accaacaaaa ccaaaactac agcaaagaga   2700
aaacttgaat atacccattg aagaaagtaa aaaaagaga aaaatggcct ttgaatttga   2760
tattaattca gatagttcag aaactactga tcttttgagc atggtttcag aagaagagac   2820
attgaaaaca ctgtataggga acaataatcc accagcttct catctttgtg tcaaaacacc   2880
aaaaaaggcc ccttcatctc taacaacccc tggacctaca ctgaagtttg gagctataag   2940
aaaaatgcgg gaggaccgtt gggctgtaat tgctaaaatg gatagaaaaa aaaaactaaa   3000
agaagctgaa aagttatttg tttaatttca gagaatcagt gtagttaagg agcctaataa   3060
cgtgaaactt atagttaata ttttgttctt atttgccaga gccacatttt atctggaagt   3120
```

-continued

```
tgagacttaa aaaatacttg catgaatgat ttgtgtttct ttatatttt agcctaaatg    3180 ttaactacat attgtctgga aacctgtcat tgtattcaga taattagatg attatatatt   3240
gttgttactt tttcttgtat tcatgaaaac tgtttttact aagttttcaa atttgtaaag   3300
ttagcctttg aatgctagga atgcattatt gagggtcatt ctttattctt tactattaaa   3360
atattttgga tgcaaaaaaa aaaaaaaaaa aaa                                3393
```

(2) INFORMATION FOR SEQ ID NO: 2:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 2:

```
gtacagcaga aagcaagcaa ctgaatg                                       27
```

(2) INFORMATION FOR SEQ ID NO: 3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 3:

```
gaaggaactg ctttagaatc caatttcc                                      28
```

(2) INFORMATION FOR SEQ ID NO: 4:

(i) SEQUENCE CHARACTERISTICS:
        (A) LENGTH: 976 amino acids
        (B) TYPE: amino acid
        (D) TOPOLOGY: linear (xi) SEQUENCE DESCRIPTION: SEQ ID NO: 4:

```
Met Glu Lys Gln Lys Pro Phe Ala Leu Phe Val Pro Pro Arg Ser Ser
 1               5                  10                  15

Ser Ser Gln Val Ser Ala Val Lys Pro Gln Thr Leu Gly Gly Asp Ser
            20                  25                  30

Thr Phe Phe Lys Ser Phe Asn Lys Cys Thr Glu Asp Asp Leu Glu Phe
        35                  40                  45

Pro Phe Ala Lys Thr Asn Leu Ser Lys Asn Gly Glu Asn Ile Asp Ser
    50                  55                  60

Asp Pro Ala Leu Gln Lys Val Asn Phe Leu Pro Val Leu Glu Gln Val
65                  70                  75                  80

Gly Asn Ser Asp Cys His Tyr Gln Glu Gly Leu Lys Asp Ser Asp Leu
                85                  90                  95

Glu Asn Ser Glu Gly Leu Ser Arg Val Phe Ser Lys Leu Tyr Lys Glu
               100                 105                 110

Ala Glu Lys Ile Lys Lys Trp Lys Val Ser Thr Glu Ala Glu Leu Arg
           115                 120                 125

Gln Lys Glu Ser Lys Leu Gln Glu Asn Arg Lys Ile Ile Glu Ala Gln
       130                 135                 140

Arg Lys Ala Ile Gln Glu Leu Gln Phe Gly Asn Glu Lys Val Ser Leu
145                 150                 155                 160

Lys Leu Glu Glu Gly Ile Gln Glu Asn Lys Asp Leu Ile Lys Glu Asn
                165                 170                 175
```

```
Asn Ala Thr Arg His Leu Cys Asn Leu Leu Lys Glu Thr Cys Ala Arg
            180                 185                 190

Ser Ala Glu Lys Thr Lys Lys Tyr Glu Tyr Glu Arg Glu Glu Thr Arg
            195                 200                 205

Gln Val Tyr Met Asp Leu Asn Asn Asn Ile Glu Lys Met Ile Thr Ala
            210                 215                 220

Phe Gln Glu Leu Arg Val Gln Ala Glu Asn Ser Arg Leu Glu Met His
225                 230                 235                 240

Phe Lys Leu Lys Glu Asp Tyr Glu Lys Ile Gln His Leu Glu Gln Glu
                245                 250                 255

Tyr Lys Lys Glu Ile Asn Asp Lys Glu Lys Gln Val Ser Leu Leu Leu
            260                 265                 270

Ile Gln Ile Thr Glu Lys Glu Asn Lys Met Lys Asp Leu Thr Phe Leu
            275                 280                 285

Leu Glu Glu Ser Arg Asp Lys Val Asn Gln Leu Glu Glu Lys Thr Lys
            290                 295                 300

Leu Gln Ser Glu Asn Leu Lys Gln Ser Ile Glu Lys Gln His His Leu
305                 310                 315                 320

Thr Lys Glu Leu Glu Asp Ile Lys Val Ser Leu Gln Arg Ser Val Ser
                325                 330                 335

Thr Gln Lys Ala Leu Glu Glu Asp Leu Gln Ile Ala Thr Lys Thr Ile
            340                 345                 350

Cys Gln Leu Thr Glu Glu Lys Glu Thr Gln Met Glu Glu Ser Asn Lys
            355                 360                 365

Ala Arg Ala Ala His Ser Phe Val Val Thr Glu Phe Glu Thr Thr Val
            370                 375                 380

Cys Ser Leu Glu Glu Leu Leu Arg Thr Glu Gln Gln Arg Leu Glu Lys
385                 390                 395                 400

Asn Glu Asp Gln Leu Lys Ile Leu Thr Met Glu Leu Gln Lys Lys Ser
                405                 410                 415

Ser Glu Leu Glu Glu Met Thr Lys Leu Thr Asn Asn Lys Glu Val Glu
            420                 425                 430

Leu Glu Glu Leu Lys Lys Val Leu Gly Glu Lys Glu Thr Leu Leu Tyr
            435                 440                 445

Glu Asn Lys Gln Phe Glu Lys Ile Ala Glu Glu Leu Lys Gly Thr Glu
            450                 455                 460

Gln Glu Leu Ile Gly Leu Leu Gln Ala Arg Glu Lys Glu Val His Asp
465                 470                 475                 480

Leu Glu Ile Gln Leu Thr Ala Ile Thr Thr Ser Glu Gln Tyr Tyr Ser
                485                 490                 495

Lys Glu Val Lys Asp Leu Lys Thr Glu Leu Glu Asn Glu Lys Leu Lys
            500                 505                 510

Asn Thr Glu Leu Thr Ser His Cys Asn Lys Leu Ser Leu Glu Asn Lys
            515                 520                 525

Glu Leu Thr Gln Glu Thr Ser Asp Met Thr Leu Glu Leu Lys Asn Gln
            530                 535                 540

Gln Glu Asp Ile Asn Asn Asn Lys Lys Gln Glu Glu Arg Met Leu Lys
545                 550                 555                 560

Gln Ile Glu Asn Leu Gln Glu Thr Glu Thr Gln Leu Arg Asn Glu Leu
                565                 570                 575

Glu Tyr Val Arg Glu Glu Leu Lys Gln Lys Arg Asp Glu Val Lys Cys
            580                 585                 590

Lys Leu Asp Lys Ser Glu Glu Asn Cys Asn Asn Leu Arg Lys Gln Val
```

```
                595                 600                 605
Glu Asn Lys Asn Lys Tyr Ile Glu Glu Leu Gln Gln Glu Asn Lys Ala
        610                 615                 620
Leu Lys Lys Lys Gly Thr Ala Glu Ser Lys Gln Leu Asn Val Tyr Glu
625                 630                 635                 640
Ile Lys Val Asn Lys Leu Glu Leu Glu Leu Glu Ser Ala Lys Gln Lys
                645                 650                 655
Phe Gly Glu Ile Thr Asp Thr Tyr Gln Lys Glu Ile Glu Asp Lys Lys
                660                 665                 670
Ile Ser Glu Glu Asn Leu Leu Glu Val Glu Lys Ala Lys Val Ile
            675                 680                 685
Ala Asp Glu Ala Val Lys Leu Gln Lys Glu Ile Asp Lys Arg Cys Gln
        690                 695                 700
His Lys Ile Ala Glu Met Val Ala Leu Met Glu Lys His Lys His Gln
705                 710                 715                 720
Tyr Asp Lys Ile Ile Glu Glu Arg Asp Ser Glu Leu Gly Leu Tyr Lys
                725                 730                 735
Ser Lys Glu Gln Glu Gln Ser Ser Leu Arg Ala Ser Leu Glu Ile Glu
            740                 745                 750
Leu Ser Asn Leu Lys Ala Glu Leu Leu Ser Val Lys Lys Gln Leu Glu
        755                 760                 765
Ile Glu Arg Glu Glu Lys Glu Lys Leu Lys Arg Glu Ala Lys Glu Asn
770                 775                 780
Thr Ala Thr Leu Lys Glu Lys Lys Asp Lys Lys Thr Gln Thr Phe Leu
785                 790                 795                 800
Leu Glu Thr Pro Glu Ile Tyr Trp Lys Leu Asp Ser Lys Ala Val Pro
                805                 810                 815
Ser Gln Thr Val Ser Arg Asn Phe Thr Ser Val Asp His Gly Ile Ser
            820                 825                 830
Lys Asp Lys Arg Asp Tyr Leu Trp Thr Ser Ala Lys Asn Thr Leu Ser
            835                 840                 845
Thr Pro Leu Pro Lys Ala Tyr Thr Val Lys Thr Pro Thr Lys Pro Lys
    850                 855                 860
Leu Gln Gln Arg Glu Asn Leu Asn Ile Pro Ile Glu Glu Ser Lys Lys
865                 870                 875                 880
Lys Arg Lys Met Ala Phe Glu Phe Asp Ile Asn Ser Asp Ser Ser Glu
                885                 890                 895
Thr Thr Asp Leu Leu Ser Met Val Ser Glu Glu Thr Leu Lys Thr
                900                 905                 910
Leu Tyr Arg Asn Asn Pro Pro Ala Ser His Leu Cys Val Lys Thr
    915                 920                 925
Pro Lys Lys Ala Pro Ser Ser Leu Thr Thr Pro Gly Pro Thr Leu Lys
    930                 935                 940
Phe Gly Ala Ile Arg Lys Met Arg Glu Asp Arg Trp Ala Val Ile Ala
945                 950                 955                 960
Lys Met Asp Arg Lys Lys Leu Lys Glu Ala Glu Lys Leu Phe Val
                965                 970                 975
```

ISOLATED NUCLEIC ACID MOLECULE WHICH ENCODES AN SCP-1 MUTEIN

RELATED APPLICATIONS

This application is a continuation in part of Ser. No. 08/892,702, filed Jul. 15, 1997, now U.S. Pat. No. 5,888,751 incorporated by reference herein.

FIELD OF THE INVENTION

The invention relates to the identification of a molecule or a marker for transformed cells, such as cancer cells. It also relates to a method for identifying molecules associated with pathological conditions, such as cancer.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding nucleic acid molecule to express the desired protein molecule.

To date, two strategies have been employed for the detection of such antigens, in e.g., human tumors. These will be referred to as the genetic approach and the biochemical approach. The genetic approach is exemplified by, e.g., dePlaen et al., Proc. Natl. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines. Transfectants are screened for the expression of tumor antigens via their ability to provoke reactions by anti-tumor cytolytic T cell clones. The biochemical approach, exemplified by, e.g., Mandelboim, et al., Nature 369: 69 (1994) incorporated by reference, is based on acidic elution of peptides which have bound to MHC-class I molecules of tumor cells, followed by reversed-phase high performance liquid chromatography (HPLC). Antigenic peptides are identified after they bind to empty MHC-class I molecules of mutant cell lines, defective in antigen processing, and induce specific reactions with cytotoxic T-lymphocytes. These reactions include induction of cytolytic T cell lines (CTLs) proliferation tumor necrosis factor (TNF) release, and lysis of target cells, measurable in an MTT assay, or a $^{51}$Cr release assay.

These two approaches to the molecular definition of antigens have the following disadvantages: first, they are enormously cumbersome, time-consuming and expensive; second, they depend on the establishment of CTLs with predefined specificity; and third, their relevance in vivo for the course of the pathology of disease in question has not been proven, as the respective CTLs can be obtained not only from patients with the respective disease, but also from healthy individuals, depending on their T cell repertoire.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647 (1991); Richard et al., J. Exp. Med. 178: 489–495 (1993); Coulie, et al., J. Exp. Med. 180: 35–42 (1994); Kawakami, et al., Proc. Natl. Acad. Sci. USA 91: 3515–3519 (1994).

Further, the methodologies supra described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607–637 (1990). It is also known that some epithelial cell type cancers are poorly susceptible to CTLs in vitro, thus precluding routine analysis. These problems have stimulated the art to develop additional methodologies for identifying cancer associated antigens.

One key methodology is described by Sahin, et al., Proc. Natl. Acad. Sci. USA 92: 11810–11913 (1995), incorporated by reference. Also, see U.S. patent applications Ser. No. 08/580,980, now U.S. Pat. No. 5,698,396 and application Ser. No. 08/479,328, filed on Jun. 7, 1995 and Jan. 3, 1996, respectively. All three of these references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., EMBO J 144: 2333–2340 (1995).

The SEREX methodology has been applied to esophageal cancer samples, and an esophageal cancer associated antigen has now been identified, and its encoding nucleic acid molecule isolated and cloned, as per U.S. patent application Ser. No. 08/725,182, filed Oct. 3, 1996, incorporated by reference herein.

The relationship between some of the tumor associated genes and a triad of genes, known as the SSX genes, is under investigation. See Sahin, et al., supra; and Tureci, et al., Cancer Res 56:4766–4772 (1996). One of these SSX genes, referred to as SSX2, was identified, at first, as one of two genes involved in a chromosomal translocation event (t(X; 18)(p 11.2; q 11.2)), which is present in 70% of synovial sarcomas. See Clark, et al., Nature Genetics 7:502–508 (1994); Crew et al., EMBO J 14:2333–2340 (1995). This gene was later found to be expressed in a number of tumor cells, and is now considered to be a tumor associated antigen referred to as HOM-MEL-40 by Tureci, et al, supra. Its expression to date has been observed in cancer cells, and normal testis only. This parallels other members of the "CT" family of tumor antigens, since they are expressed only in cancer and testis cells. Crew et al. also isolated and cloned the SSX1 gene, which has 89% nucleotide sequence homology with SSX2. See Crew et al., supra. Additional work directed to the identification of SSX genes has resulted in the identification of SSX3, as is described by DeLeeuw, et al., Cytogenet. Genet 73:179–183 (1996). The fact that SSX presentation parallels other CT antigens suggested to the inventors that other SSX genes might be isolated.

Application of a modification of the SEREX technology described supra has been used, together with other techniques, to clone two, additional SSX genes, referred to as SSX4 and SSX5 as well as an alternate splice variants of the SSX4 gene. This work is described in U.S. Ser. No. 08/851,138, filed May 5, 1997, incorporated by reference, as well as by Chen, et al., Proc. Natl. Acad. Sci USA 94: 1914–1918 (1997), also incorporated by reference.

The fact that many markers were found in both normal testis and tumor cells, but not other normal cells, suggested that further investigation in this area might uncover additional related molecules. The diversity of those discovered so far, however, did not provide any guidance as to the characteristics of the additional molecules which might be found.

Most of the work prior to the invention disclosed herein, used cDNA libraries obtained from cancer cells. As will be developed herein, it has now been shown that such molecules can also be determined using a non-transformed, or normal cell source for the cDNA libraries previously obtained from cancer cells. This is quite surprising, as it might well be assumed that tumor markers are expressed only in tumor cells. This has now been shown to not be the case. Exemplary of a normal cell library which can be used is a testis cell library screened against various serum samples, such as autologous serum.

The SEREX methodology, as described supra, has proven to be very useful in identifying molecules of interest. The inventors have found, however, that it is not an ideal method when short cDNA molecules are the ones of interest in a given library. One aspect of the invention described herein is a method for identifying short cDNA molecules which are of interest in connection with pathologies of the type discussed herein.

Synaptonemal complex protein 1 ("SCP1" hereafter) is a protein involved in the meiotic prophase of spermatocytes. The gene which encodes murine SCP1 has been mapped to chromosome 1p.12-p.13. See Sage, et al, Biochem. Biophys. Acta 1263: 258–260 (1995) incorporated by reference. The human form of SCP1 has been reported to be expressed only in testis. See Meuwissen, et al, EMBO J 11:5091–5100 (1992), incorporated by reference.

Meuwissen et al, supra describe SCP1 protein as a major component of the synaptonemal complex, a tripartite, macromolecular assembly which is formed between homologous chromosomes during meiotic prophase. See Wettstein, et al, Annu. Rev. Genet 3:331–413 (1984); Heyting, et al, Genome 31:81–89 (1986). More details of the protein may be found e.g., in Meuwissen, et al, Genomics 37:101–106 (1997); Gillies, et al, Curr. Trac. Lab. Carlsberg 40:135–161 (1975); Schmekel, et al, Exp. Cell Res 226:20–30 (1996); Moses, et al, Symp. Soc. Exp. Biol. 38:245–270 (1984); Carpenter, Bioessays 6:232–236 (1987); Loidl, et al, Genome 33:759–778 (1990); Moens, Bioessays 16:101–106 (1994); Roeder, Trends Genet 6:385–389 (1990).

The location of the gene for SCP1 is different than that for all previously identified cancer testis antigens (CTAs), which map to the X chromosome.

It has been found, that SCP1 is expressed in tumor cells, especially in renal cell carcinomas, gliomas, and breast carcinomas, but not in normal cells except for testis. Hence, it serves as a CTA but differs in that it is expressed strongly not only in melanoma, but in those tumor types listed supra.

This is significant in terms of both diagnostic and therapeutic approaches to transformed cells, as will be seen from the disclosure which follows. The fact that the molecule is also involved in normal meiosis suggests an important correlation between the molecule, chromosomal replication, cell division, and the onset of oncogenesis.

DETAILED DESCRIPTION OF PREFERRED EMBODIMENTS

Example 1

Experiments were carried out to identify and to isolate cDNA corresponding to mRNA found exclusively in testis, and hence genes expressed only in testis cells. To do this, the methodology described by Diatchenko et al, Proc. Natl. Acad. Sci USA 93:6025–6030 (1996), incorporated by reference, was used to generate cDNA fragments specifically expressed in human testis cells, which had been obtained from biopsies of tumor free patients. Specifically, two mg of mRNA was taken from each of two, different testicular tissue specimens, and was used as a tester probe. Driver cDNA was obtained by synthesizing cDNA from mRNA taken from ten healthy tissue specimens (colon, stomach, brain, resting and activated peripheral blood mononuclear cells, skeletal muscle, liver, kidney, lungs and skin). Diatchenko, et al, supra, was followed to carry out suppression subtractive hybridization PCR, after tester and driver cDNA were permitted to hybridize. The resulting, isolated fragments were then used to isolate full length transcript. To do this, a cDNA phagemid library was constructed, using the same cDNA (i.e., the normal testis library), using 5 mg of mRNA. A library of $4 \times 10^6$ primary clones was produced and, following standard isolation procedures, the phagemid library was hybridized onto nitrocellulose membranes and then blotted with the fragments obtained previously. Following blotting, the membranes were washed, and any phagemids which had bound to immobilized cDNA were eluted. The eluted, full length molecules were used to prepare double stranded cDNA, using known methods, and the cDNA was then re-ligated into precut vectors, and then used for transfections and amplification. An expression library of 400,000 recombinants resulted.

Example 2

Following the creation of the expression library described supra, immune screening experiments were carried out to determine if any IgGs against the expression products of the library were present in serum from a tumor patient. To do this, a serum sample of a patient with renal cell cancer was diluted, 1:100, and then screened against 200,000 of the recombinants, following Türeci, et al, Cancer Res 56:4766–4772 (1996), and U.S. Pat. No. 5,698,396, both of which are incorporated by reference. Reactive clones were visualized by incubation with an anti-human, Fc specific, alkaline phosphatase labelled antibody, which was then developed with the dye 5-bromo-4-chloro-3-indolyl phosphate, and nitroblue tetrazolium, following known methods. Of the 200,000 clones screened, five were positive. Three of these were found to be identical to part of a previously identified protein, i.e., SCP1, a protein whose expression has been linked, specifically to the meiotic prophase of spermatocytes, and which has been linked to the pairing of homologous chromosomes, which is essential to the generation of haploid cells in meioses I. The three positive clones were sequenced and found to correspond to nucleotides 726–2401, 147–2728, and 634–2462 of SCP1, but for changes at amino acid positions 225 where CAT was replaced by TTT leading to F instead of H, and at position 226, glycine was replaced by glutamine (GGG was replaced by GAG). This represents changes at nucleotides 716, 767, 768 and 771. There is a change at position 208, but it is a silent mutation. The sequence of SCP1 is set forth as SEQ ID NO: 1 and is found in Meuwissen et al., Genomics 37: 101–106 (1997) incorporated by reference. The amino acid sequence described herein (with three changed is provided as SEQ ID NO: 4.

Example 3

Experiments were then carried out to determine whether or not the SCP1 molecule was being expressed by normal tissues. This was determined via Northern blotting, and via RT-PCR. Northern blotting followed Chomczynsky, et al. Anal. Biochem 72:248–254 (1976), incorporated by reference. To elaborate, mRNA was removed from various tissue samples, checked for integrity via electrophoresis in formalin/MOPS gels, and then 10 mg from each sample were blotted onto nylon membranes, prehybridized, and then incubated with a $^{32}$P labelled cDNA probe which consisted of nucleotides 2715–3264 of SCP1 (SEQ ID NO: 1). Specifically the probes were hybridized overnight at 42° C. in a solution of 50% formamide 6×SSC, 5×Denhardt's, and 0.2% SDS. Membranes were then washed at progressively higher stringencies, with the final wash at 1×SSC, 0.2% SDS at 65° C. Autoradiography was conducted at −70° C., for up to 7 days.

To carry out RT-PCR, total RNA was extracted, primed with an oligo-dT (18) nucleotide, and then reverse transcribed. Primers used were:

5'-GTACAGCAGA AAGCAAGCAA CTGAATG     (SEQ ID NO:2)

and

5'-GAAGGAACTG CTTTAGAATC CAATTTCC-3' (SEQ ID NO:3).

The expected primer product size was 564 base pairs.

The only normal tissue sample to test positive was testis.

The RT-PCR protocol set forth supra was also used on tumor tissue samples. These results are set forth in the Table which follows. Northern blotting confirmed the work for renal, breast, and glioma tumor samples.

| Tumor Type | SCP1 Expression (positive/number tested) |
| --- | --- |
| melanoma | 4/28 |
| breast cancer | 9/33 |
| colorectal carcinoma | 0/32 |
| prostate cancer | 0/27 |
| glioma | 6/15 |
| gastric carcinoma | 1/10 |
| thyroid cancer | 0/5 |
| lymphoma or leukemia | 0/14 |
| lung carcinoma (NSCLC) non-small cell | 1/14 |
| renal cell carcinoma | 3/36 |
| ovarian carcinoma | 3/12 |
| seminoma | 0/2 |
| endometrial carcinoma | 0/8 |
| sarcoma | 0/4 |

Example 4

The analysis discussed, supra, was carried forward with Southern blotting, in accordance with Maniatis, et al, Molecular Cloning: A Laboratory Manual (Cold Spring Harbor Laboratory, 1982). In brief, the endonuclease Hae III was used on DNA extracted from testis and peripheral blood lymphocytes. Equal amounts of sample were checked by staining, visualized under UV light, and then were hybridized with full length cDNA for SCP1 at 6×SSC, 4× Denhardt's and 0.5% SDS, followed by washing and autoradiography as described above.

The banding patterns which resulted suggested a gene family, rather than a single gene.

Example 5

A final set of experiments was then carried out to test for presence of the SCP1 protein. This was done by Western blotting. SCP1 specific rabbit antiserum, described by Schmekel et al, Chromosoma 102: 682–692 (1993), incorporated by reference, was used. Cell lysates (10 ug, per lane), were mixed with 2×SDS sample buffer (0.1 M Tris-HCl, pH 6.8, 0.2M dithiothreitol, 4% SDS, 0.2% bromophenol blue, 20% glycerol), electrophoresed on 12% SDS gels, via PAGE, and were then blotted to nylon membranes. The membranes were blocked with 5% non-fat milk in TBS for 1 hour, to address non-specific binding, and the membranes were then incubated with 1:100 diluted rabbit-anti SCP1 antiserum. The blots were then incubated for 1 hour with alkaline phosphatase conjugated anti-IgG. Membranes were washed extensively with TBS and 0.01% Tween, following each incubation. Positive reactions were monitored in the same fashion as is described, supra.

A 125 kDa protein was detected in lysates of normal testis cells and tumor cells, but in no other samples, indicating that SCP1 functions as a marker for tumor cells.

Example 6

The amino acid sequence of the protein encoded by the SCP-1 gene was analyzed for peptide sequences which correspondence to HLA binding motifs. This was done using the algorithm taught by Parker et al., J. Immunol. 142: 163 (1994), incorporated by reference. In the Table which follows, the amino acid sequence, the HLA molecule to which it presumably binds, and the positions in SCP-1 are given. The resulting complexes should provoke a cytolytic T cell response. This could be determined by one skilled in the art following methods taught by, e.g., van der Bruggen, et al., J. Eur. J. Immunol. 24: 3038–3043 (1994), incorporated by reference.

| MHC MOLECULE | PEPTIDE | POSITION (SEQ ID NO: 4) |
| --- | --- | --- |
| A1 | NSEGLSRVY | 98-106 |
| A1 | SSELEEMTK | 416-424 |
| A1 | EVELEELKK | 430-438 |
| A1 | CTEDDFEFPF | 41-50 |
| A1 | NIDSDPALQK | 11-70 |
| A1 | RTEQQRLENY | 392-401 |
| A1 | IADEAVKLQK | 685-694 |
| A1 | IAEMVALMEK | 704-713 |
| A2 | KLYKEAEKI | 108-116 |
| A2 | KLQENRKII | 133-141 |
| A2 | KMITAFEEL | 220-228 |
| A2 | VVTEFETTV | 376-384 |
| A2 | VELEELKKV | 431-439 |
| A2 | VLGEKETLL | 439-447 |
| A2 | LLQAREKEV | 470-478 |
| A2 | RMLTQIENL | 554-562 |

| MHC MOLECULE | PEPTIDE | POSITION (SEQ ID NO: 4) |
|---|---|---|
| A2 | NLQETETQL | 561-569 |
| A2 | QLNVYEIKV | 632-640 |
| A2 | NLLEEVEKA | 674-682 |
| A2 | KRJREDRWAV | 947-955 |
| A2 | ALQKVNFLPV | 67-76 |
| A2 | FLLEESRDKV | 287-296 |
| A2 | KLTHJKEVEL | 424-433 |
| A2 | KQFEKIAEEL | 451-460 |
| A2 | GLLQAREKEV | 469-478 |
| A2 | TQLRNELEYV | 567-576 |
| A2 | KQVENKNKYI | 603-612 |
| A2 | KQLNVYEIKV | 631-640 |
| A2 | NVYEIKVNKL | 634-643 |
| A2 | YLWTSAKNTL | 835-844 |
| A2 | KLKEAEKLFV | 964-973 |
| A3 | KLSSKRELK | 502-510 |
| A3 | NLRKQVENK | 600-608 |
| A3 | TLGGDSTFFK | 27-36 |
| A3 | KLYKEAEKIK | 108-117 |
| A3 | KMITAFEELR | 220-229 |
| A3 | LLYDNKQFEK | 446-455 |
| A3 | KLELELESAK | 642-651 |
| A3 | LLETPDJYWK | 797-806 |
| A24 | VYMDLNSNI | 210-218 |
| A24 | NYEDQLIIL | 400-408 |
| A24 | VYEIKVNKL | 635-643 |
| A24 | LYDNKQFEKI | 447-456 |
| B7 | AQRKAIQEL | 143-151 |
| B7 | ATRHLCNLL | 178-186 |
| B7 | TPKKAPSSL | 925-933 |
| B7 | DPALQKVNFL | 65-74 |
| B7 | QAREKEVHDL | 472-481 |
| B7 | LPKRGQRPKL | 494-503 |
| B7 | RPKLSSKREL | 500-509 |
| B7 | KPKLQQRENL | 859-868 |
| B8 | ELRQKESKL | 126-143 |
| B8 | ESRDKVNQL | 291-299 |
| B8 | SAKQKFGEI | 649-657 |
| B8 | ISKDKRDYL | 828-836 |
| B8 | IAKMDRKKKL | 956-965 |
| B35 | ISKDKRDY | 828-835 (8MER) |
| B35 | TPKKAPSSL | 925-933 |
| B35 | LPKRGQRPKL | 494-503 |
| B35 | RPKLSSKREL | 500-509 |
| B35 | KSKEQEQSSL | 733-742 |
| B35 | KPKLQQRENL | 859-868 |
| B44 | TEDDFEFPF | 42-50 |
| B44 | KEAEIKKW | 111-119 |
| B44 | AEKTKKYEY | 194-202 |
| B44 | TEQQRLENY | 393-401 |
| B44 | RELKNTEYF | 507-515 |
| B44 | AESKQLNVY | 628-636 |
| B44 | EEETLKTLY | 903-911 |
| B44 | YEREETRQVY | 202-211 |
| B44 | AENSRLEMHF | 232-241 |
| B44 | KENKMKDLTF | 278-287 |
| B44 | REKEVHDLEY | 474-483 |
| B44 | KEVHDLEYSY | 476-485 |
| B44 | DEVKCKLDKS | 585-594 |
| B44 | LELESAKQKF | 645-654 |
| B44 | EERKSELGLY | 723-732 |
| B44 | SEEETLKTLY | 902-911 |
| B52 | KQKPFALFV | 3-11 |
| B52 | LQIAINTIC | 345-353 |
| B52 | ENYEDQLII | 399-407 |
| B52 | CQHKIAEMV | 700-708 |
| B52 | LQKVNFLPVL | 68-77 |

The foregoing examples demonstrate several features of the invention. These include diagnostic methods for determining presence of transformed cells, such as cancer cells, in a sample. The examples show that there is a family of SCP genes, which includes SCP-1. Hence, the invention involves, inter alia, detecting an SCP protein or mRNA for an SCP gene in a sample taken from a source other than testis, wherein presence of either or both of these is indicative of a pathology, such as cancer or some other type of transformed cells. Exemplary of the type of diagnostic assays which can be carried out are amplification assays such as polymerase chain reaction, or immunoassays. It is especially preferred to assay for SCP-1, as a determination of breast cancer, ovarian cancer, renal cell carcinoma, or glioma.

The SCP proteins, as indicated, have been associated, exclusively, with meiosis. As a rule, cells other than germ cells do not undergo meiosis. Hence, the expression of SCP proteins such as SCP-1 in a context other than germ cells undergoing meiosis is clearly an indication of an abnormality. It is believed that expression of SCP proteins may contribute to the genetic instability of cancer cells, leading to abnormalities such as aneuploidy, manifesting the phenomenon in early neoplastic change. One aspect of the invention, then, is a method for determining presence of an abnormal condition by assaying for an SCP protein, or a peptide derived from the protein, wherein the presence of the protein at all, or an abnormal level of the protein (which may include its presence), is indicative of an abnormality, such as cancer. There are many ways to carry out this type of assay. For example, as indicated herein, antibodies to the protein were found in patient samples. One can assay for these antibodies using, e.g., the methodology described herein, or by using a purified SCP protein or antigenic fragment thereof, and so forth. One can also assay for the protein itself, using antibodies, which may be isolated from samples, or generated using an SCP protein and standard techniques. This antibodies can then be labelled, if desired, and used in standard immunoassays.

Similarly, any and all nucleic acid hybridization systems can be used, including amplification assays, such as PCR, basic probe hybridization assays, and so forth. The antibodies, such as polyclonal antibodies, monoclonal antibodies, the hybridomas which produce them, recombinantly produced antibodies, binding fragments of these, hybridization kits, DNA probes, and so forth, are all additional features of the invention.

Any one of these can also be used in progression/regression studies. Since it is clear that a low or non-existent level of expression of SCP protein is found in normal cells, one can monitor the course of abnormality involving expression of SCP, simply by monitoring levels of the protein, its expression, and so forth using any or all of the methods set forth supra.

It should be clear that these methodologies may also be used to track the efficacy of a therapeutic regime. Essentially, one can take a baseline value for the SCP protein or proteins being tested, using any of the assays discussed supra, administer a given therapeutic agent, and then monitor levels of the protein thereafter, observing changes in SCP levels as indicia of the efficacy of the regime.

Regarding the progression/regression studies, one can monitor the course of an abnormality involving expression of SCP-1 simply by monitoring levels of protein, its expression, antibodies against it and so forth using any or all of the methods set forth supra.

It should be clear that these methodologies may also be used to track the efficacy of a therapeutic regime. Essentially, one can take a baseline value for the SCP-1 protein, using any of the assays discussed supra, administer a given therapeutic agent, and then monitor levels of the protein, using any of the assays discussed supra, administer a given therapeutic agent, and then monitor levels of the protein thereafter, observing changes in SCP-1 levels as indicia of the efficacy of the regime.

One can monitor these levels using, e.g., tetrameric peptide structures, such as structures based on the disclosures of Brand, et al., Nature 391 795–799 (1998); Altman, et al., Science 274: 94–96 (1996), and U.S. patent application Ser. No. 09/049,850, filed Mar. 27, 1998, all of which are incorporated by reference.

The identification of SCP proteins as being implicated in pathological conditions such as cancer also suggests a number of therapeutic approaches to such conditions. The experiments set forth supra establish that antibodies are produced in response to expression of the protein, suggesting its use as a vaccine. Hence, a further embodiment of the invention is the treatment of conditions which are characterized by aberrant or abnormal levels of one or more SCP proteins, via immunotherapeutic approaches. One of these approaches is the administration of an amount of an SCP protein, or an immunogenic peptide derived from the protein in an amount sufficient to provoke or augment an immune response. The protein or peptide may be combined with one or more of the known immune adjuvants, costimulatory molecules, or MHC helper binding peptides, such as saponins, GM-CSF, interleukins, LIF-3, emulsifying oils such as vitamin E, heat shock proteins and so forth. If the peptides are too small to generate a sufficient antibody response, they can be coupled to the well known conjugates used to stimulate responses.

Similarly, the immunotherapeutic approaches include administering an amount of inhibiting antibodies sufficient to inhibit the SCP protein. These antibodies may be, e.g., antibodies produced via any of the standard approaches elaborated upon supra.

T cell responses may also be elicited by using peptides derived from the SCP proteins which then complex, non-covalently, with MHC molecules, thereby stimulating proliferation of cytolytic T cells against any such complexes in the subject. It is to be noted that the T cells may also be elicited in vitro using immune responsive cells such as dendritic cells, lymphocytes, or any other immune responsive cells, and then reperfused into the subject being treated.

Note that the generation of T cells and/or antibodies can also be accomplished by administering cells, preferably treated to be rendered non-proliferative, which present relevant T cell or B cell epitopes for response.

The therapeutic approaches may also include gene therapies, wherein an antisense molecule, preferably from 10 to 100 nucleotides in length, is administered to the subject either "neat" or in a carrier, such as a liposome, to facilitate incorporation into a cell, followed by inhibition of expression of the protein. Such antisense sequences may also be incorporated into appropriate vaccines, such as in viral vectors (e.g., Vaccinia), bacterial constructs, such as variants of the well known BCG vaccine, and so forth.

An additional DNA based therapeutic approach is the use of a vector which comprises one or more nucleotide sequences, preferably a plurality of these, each of which encodes an immunoreactive peptide derived from the expressed proteins. One can combine these peptide expressing sequences in all possible variations, such as one from each protein, several from one or more protein and one from each of the additional proteins, a plurality from some and none from others, and so forth.

Other therapeutic approaches include the administration of SCP-1 proteins per se, one or more antigenic peptides derived therefrom, such as those presented in Example 6, as well as so-called polytopic vaccines. These include a plurality of antigenic peptides, such as those in Example 6, united together, preferably by linker sequences. The resulting peptides may bind to either MHC-Class I or Class II molecules. These proteins, peptides, or polytopic vaccines may be administered in combination with an appropriate adjuvant, costimulatory molecule, or binding helper peptide. They may also be administered in the form of genetic constructs which are designed to permit expression of the protein, the peptide, the polytopic structures, etc. Peptides and polytopic structures can be expressed by so-called "minigenes" i.e., DNA molecules designed to express portions of the entire SCP-1 molecule, or the various portions of the molecules, linked together as described supra.

The amount of agent administered and the manner in which it is administered will, vary, based on the condition being treated and the individual. Standard forms of administration, such as intravenous, intradermal, subcutaneous, oral, rectal and transdermal administration can be used. With respect to formulations, the proteins and or peptides may be combined with adjuvant and/or carriers such as a saponin, GM-CSF, one or more interleukin, vitamin E, FLT-3, one or more heat shock protein, etc.

When the nucleic acid approach is utilized, various vectors, such as Vaccinia or adenovirus based vectors can be used. Any vector useful in eukaryotic transfection, such as in transfection of human cells, can be used. These vectors can be used to produce, e.g., cells such as dendritic cells which present relevant peptide/MHC complexes on their surface. The cells can then be rendered non-proliferative prior to their administration, using standard methodologies.

Polytopes, as used herein, are groups of two or more potentially immunogenic or immune stimulating peptides, which can be joined together in various ways, to determine if this type of molecule will stimulate and/or provoke an immune response.

These peptides can be joined together directly, or via the use of flanking sequences. See Thompson et al. Proc. Natl. Acad. Sci USA 92(13): 5845–5849 (1995), teaching the direct linkage of relevant epitopic sequences. The use of polytopes as vaccines is well known. See, e.g., Gilbert et al., Nat Biotechnol. 15(12): 1280–1284 (1997); Thomson et al., supra; Thomson et al., J. Immunol. 157(2): 822–826 (1996); Tam et al., J. Exp. Med. 171(1): 299–306 (1990), all of which are incorporated by reference. The Tam reference in particular shows that polytopes, when used in a mouse model, are useful in generating both antibody and protective immunity. Further, the reference shows that the polytopes, when digested, yield peptides which can be and are presented by MHCs. Tam shows this by showing recognition of individual epitopes processed from polytope 'strings' via CTLs. This approach can be used, e.g., in determining how many epitopes can be joined in a polytope and still provoke recognition and also to determine the efficacy of different combinations of epitopes. Different combinations may be 'tailor-made' for the patients expressing particular subsets of tumor rejection antigens. These polytopes can be introduced as polypeptide structures, or via the use of nucleic acid delivery systems. To elaborate, the art has many different ways available to introduce DNA encoding an individual epitope, or a polytope such as is discussed supra. See, e.g., Allsopp et al., Eur J. Immunol. 26(8); 1951–1959(1996), incorporated by reference. Adenovirus, pox-virus, Ty-virus like particulars, plasmids, bacteria, etc., can be used. One can test these systems in mouse models to determine which system seems most appropriate for a given, parallel situation in humans. They can also be tested in human clinical trials.

Also a feature of the invention are the mutein forms of SCP-1 and the nucleic acid molecule encoding it, as described supra. These muteins can be used in the same way SCP molecules can be used.

The invention also involves a method for determining substances produced by a subject capable of eliciting an immune response, wherein one produces a cDNA library of a normal cell taken from a subject, such as a testis cell, inserting the cDNA molecules of the library into an expression vector, transfecting the vector into host cells to produce transfected host cells and then culturing the transfected host cell to express the substance of interest. Following this, the cells are lysed to form a lysate, which is then contacted with a sample of a body fluid taken from a subject, which contains an immunologic binding partner for the immunoreactive substance. This step removes any immunologic binding partner from said sample which is specific for non-transfected host cells. The resulting sample is then contacted to a sample of lysed host cells transfected with the same vector which does not contain any library cDNA which removes any immunologic binding partners specific for vector produced antigens. Then, the sample is contacted to the lysate so that any binding partners specific substance bind thereto, after which one determines whether or not any binding partners have, in fact, bound to such substances, so as to determine said immunoreactive substance. This method is similar to that described in U.S. Pat. No. 5,698,396, except that the source of the library is a normal cell, such as a testis cell. As the examples, supra, indicate, this type of library was used to identify the tumor antigen. The body fluid sample may be taken from the same subject from whom the testis cells are taken (autologous serum), or it may be from a different individual. As in the 08/580,980 application, the cDNA so identified may be isolated, as can the binding partner. Relevant host cells for transformation may be eukaryotic, or prokaryotic, such as *E. coli*, and the expression vectors may be any of the standard expression vectors, such as a viral vector, a phage vector, and so forth. The sample used may be any of the sample types used in biological analysis, such as serum, blood cerebrospinal fluid, urine, stool samples, tissue samples such as skin, and so forth. Various types of antigens can be identified in this way, such as cancer associated antigens, autoimmune antigens, antigen associates with pathogens, such as viruses, and so forth. The methodology is conveniently carried out by, inter alia, immobilizing the lysate described supra to, e.g., a membrane, such as a nylon or a cellulose membrane.

Other features of the invention will be clear to the skilled artisan, and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. An isolated nucleic acid molecule which encodes a mutein of SCP-1, said mutein consisting of the amino acid sequence of SEQ ID NO: 1 with the provisos that His at position 225 is replaced by Phe, and Gly at position 226 is replaced by Gln.

* * * * *

UNITED STATES PATENT AND TRADEMARK OFFICE
CERTIFICATE OF CORRECTION

PATENT NO.     : 6,232,460 B1
DATED          : May 15, 2001
INVENTOR(S)    : Türeci et al.

Page 1 of 1

It is certified that error appears in the above-identified patent and that said Letters Patent is hereby corrected as shown below:

Column 6,
Line 58, change "11-70" to -- 61-70 --

Column 7,
Line 8, change "KRJREDRWAV" to -- KMREDRAWAV --
Line 23, change "LLETPDJYWK" to -- LLETPDIYWK --

Column 9,
Line 5, change "Brand" to -- Braud --

Signed and Sealed this

Twenty-ninth Day of January, 2002

Attest:

Attesting Officer

JAMES E. ROGAN
*Director of the United States Patent and Trademark Office*